United States Patent
Fu et al.

(10) Patent No.: US 11,802,861 B2
(45) Date of Patent: Oct. 31, 2023

(54) VERIFICATION METHOD OF ALLELOPATHIC INHIBITION MECHANISM BASED ON ECOLOGICAL STOICHIOMETRIC EQUILIBRIUM INTERFERENCE

(71) Applicant: JIANGSU UNIVERSITY, Zhenjiang (CN)

(72) Inventors: Weiguo Fu, Zhenjiang (CN); Yu Dong, Zhenjiang (CN); Li Zhang, Zhenjiang (CN)

(73) Assignee: JIANGSU UNIVERSITY, Zhenjiang (CN)

( * ) Notice: Subject to any disclaimer, the term of this patent is extended or adjusted under 35 U.S.C. 154(b) by 112 days.

(21) Appl. No.: 17/597,089

(22) PCT Filed: Jan. 15, 2021

(86) PCT No.: PCT/CN2021/072044
§ 371 (c)(1),
(2) Date: Dec. 24, 2021

(87) PCT Pub. No.: WO2022/099924
PCT Pub. Date: May 19, 2022

(65) Prior Publication Data
US 2023/0058807 A1    Feb. 23, 2023

(30) Foreign Application Priority Data
Nov. 13, 2020  (CN) .......................... 202011267193.9

(51) Int. Cl.
*A01B 79/02* (2006.01)
*G01N 33/00* (2006.01)
*G01N 33/24* (2006.01)

(52) U.S. Cl.
CPC ......... *G01N 33/0098* (2013.01); *G01N 33/24* (2013.01)

(58) Field of Classification Search
CPC ........................... G01N 33/0098; G01N 33/24
See application file for complete search history.

(56) References Cited

U.S. PATENT DOCUMENTS

2013/0157860 A1    6/2013    Inaba

FOREIGN PATENT DOCUMENTS

| CN | 105766284 A | 7/2016 |
|---|---|---|
| CN | 105784613 A | 7/2016 |
| CN | 107328908 A | 11/2017 |

OTHER PUBLICATIONS

Zhao-Hui Li, Qiang Wang, Xiao Ruan, Cun-De Pan and De-An Jiang, "Phenolics and Plant Allelopathy," Dec. 7, 2010, Molecules 2010, 15, pp. 8933-8952. (Year: 2010).*

Fu Weiguo, et al., Effects on Growth Indexes of Phalaris arundinacea by Allelopathy of Phragmites australis Decaying Substance in Riverside Wetlands in Zhenjiang, Wetland Science, 2015, pp. 118-123, vol. 13, No. 1.

* cited by examiner

*Primary Examiner* — Kyle R Quigley
*Assistant Examiner* — Christine Y Liao
(74) *Attorney, Agent, or Firm* — Bayramoglu Law Offices LLC

(57) ABSTRACT

A verification method of an allelopathic inhibition mechanism based on ecological stoichiometric equilibrium interference is disclosed. By taking ecological stoichiometric characteristics and growth characteristics of *Phalaris arundinacea* under an equilibrium state as a control, a relative coefficient of variation (RCv) is used to characterize an interference intensity of different intensities of allelopathic stress on ecological stoichiometric equilibrium of the *P. arundinacea* and an inhibitory intensity of different intensities of allelopathic stress on growth of the *P. arundinacea*. Then, through correlation analysis among parameters including the intensity of the allelopathic stress, the ecological stoichiometric equilibrium interference, and growth inhibition, a method is provided to verify whether a new mechanism of allelopathic inhibition based on the ecological stoichiometric equilibrium interference exists.

1 Claim, No Drawings

VERIFICATION METHOD OF ALLELOPATHIC INHIBITION MECHANISM BASED ON ECOLOGICAL STOICHIOMETRIC EQUILIBRIUM INTERFERENCE

CROSS REFERENCE TO THE RELATED APPLICATIONS

This application is the national phase entry of International Application No. PCT/CN2021/072044, filed on Jan. 15, 2021, which is based upon and claims priority to Chinese Patent Application No. 202011267193.9, filed on Nov. 13, 2020, the entire contents of which are incorporated herein by reference.

TECHNICAL FIELD

The present invention relates to a verification method of an allelopathic inhibition mechanism based on ecological stoichiometric equilibrium interference, and belongs to the field of interspecies competition in community ecology.

BACKGROUND

The ecological stoichiometric equilibrium theory is an important theory explaining population dynamics and community stability in the ecological stoichiometry. The ecological stoichiometric equilibrium includes not only the equilibrium of contents of carbon (C), nitrogen (N), and phosphorus (P) in plants, but also the equilibrium of the ratios of C/N, C/P, and N/P. This theory believes that organisms can grow normally only if they maintain their ecological stoichiometric equilibrium; otherwise, their growth will be abnormal and even they will die. However, the ability of organisms to maintain their own ecological stoichiometric equilibrium is often limited. Some changes in the external environment often lead to the mismatch between the balanced demand of plant for nutrients and nutrient supply of the environment, and it will inhibit the normal growth of the plant by interfering with its ecological stoichiometric equilibrium, and even lead to its degradation.

For allelopathic receptor plants, when they are under allelopathic stress, it means that their external environment has changed. In addition, some studies have found that certain allelopathic plants often restrict the absorption of N and/or P by receptor plants through the release of phenolic acid allelochemicals. Therefore, it is reasonable to infer that these allelopathic plants are very likely to inhibit the growth of the receptor plants through a way of releasing allelochemicals, restricting nutrient absorption of receptor plants, inducing nutrient mismatch of receptor plants, interfering with ecological stoichiometric equilibrium of receptor plants, and inhibiting growth of receptor plants, that is, the allelopathic stress may inhibit the growth of the receptor plants by interfering with their ecological stoichiometric balance. If so, another new mechanism of the allelopathic inhibition will be revealed. Then what methods and what experimental materials can be used to verify whether this new mechanism exists?

*P. arundinacea* and *P. australis* are both highly competitive rhizome clone plants of Gramineae, and they often establish the single *P. arundinacea* community or *P. australis* community in some natural wetlands respectively. However, some studies have shown that a vegetation succession sequence in the Zhenjiang Waterfront Wetlands along mid-lower reaches of the Yangtze River in China is as follows: a bare beach, a *P. arundinacea* community, a *P. arundinacea-P. australis* community, and a *P. australis* community. That is, in the process, the *P australis* community can replace the *P. arundinacea* community through interspecies competition. The further studies have found that it is by the release of the phenolic acid allelochemicals that the *P. australis* inhibits the growth of the *P. arundinacea* and then replaces the *P. arundinacea* community. Therefore, the present invention selects the *P. australis* with strong intensity of allelopathic stress as the allelopathic donor plant and the *P. arundinacea* as the allelopathic receptor plant to verify whether a new mechanism of the allelopathic inhibition based on the ecological stoichiometric equilibrium interference exists, so as to provide a verification method of the allelopathic inhibition mechanism based on the ecological stoichiometric equilibrium interference.

SUMMARY

Technical problem: the present invention is to verify whether a new mechanism of allelopathic inhibition based on ecological stoichiometric equilibrium interference exists by testing release of phenolic acid allelochemicals from *P. australis* in a *P. arundinacea-P. australis* community, and interference of these phenolic acid allelochemicals on ecological stoichiometric equilibrium of the *P. arundinacea* and inhibition of these phenolic acid allelochemicals on growth of the *P. arundinacea*. Therefore, the present invention can provide a new method for exploring new mechanisms of allelopathic inhibition.

Technical solution: to achieve the above objective, the present invention includes the following steps:

(1) Plot Selection:

first, selecting 2-3 plots with obvious density gradients from a *P. arundinacea-P. australis* community in waterfront wetlands along mid-lower reaches of the Yangtze River in China according to a density of the *P. australis* from low to high, where the plots represent different intensities of allelopathic stress exerted by the *P. australis* on the *P. arundinacea* from weak to strong respectively; then selecting another plot from a single *P. arundinacea* community as a control under no allelopathic stress; and setting 3 quadrats with an area of 1 $m^2$ in each plot as 3 repetitions;

(2) Parameter Measurement:

conducting the parameter measurement in late April when both the *P. arundinacea* and the *P. australis* are in a vigorous growth period, and the allelopathic stress of the *P. australis* on the *P. arundinacea* is most obvious at this time, where measurement parameters include a content of phenolic acid allelochemicals released from the allelopathic donor *P. australis* into soil, contents of organic C, N, and P in leaves of the allelopathic receptor plant *P. arundinacea*, and above-ground biomass per plant of the *P. arundinacea;* determination of the contents of C, N, and P in the leaves of the *P. arundinacea*: selecting 5-7 *P. arundinacea* plants with uniform growth in each quadrat, acquiring 3-5 unfolded leaves from top to bottom, taking the unfolded leaves back to a laboratory, and measuring the contents of C, N, and P in the leaves, where the organic C, total N, and total P are measured by potassium dichromate oxidation-spectrophotometry, Kjeldahl method, and alkali fusion-molybdenum antimony antispectrophotometry respectively;

determination of the biomass: selecting another 8-10 *P. arundinacea* plants with uniform growth in each quadrat, harvesting above-ground parts and weighing fresh weight of the above-ground parts, and then calculating average above-ground biomass per plant of the *P. arundinacea*, where the above-ground biomass per plant of the *P. arundinacea* under different intensities of allelopathic stress is obtained; and determination of a content of total phenolic acids in soil: taking 3-5 soil sampling points in each quadrat, drilling soil samples of 0-30 cm soil layer with soil at each point (roots of the *P. arundinacea* are mostly distributed here), taking the soil samples back to the laboratory, and measuring the content of the total phenolic acids in soil by phosphomolybdic acid phosphotungstate colorimetry;

(3) Analysis of Ecological Stoichiometric Equilibrium Interference;

1) Characteristics of the Ecological Stoichiometric Equilibrium and Growth of *P. arundinacea* Under Equilibrium State under the following condition: in the single *P. arundinacea* community, the ecological stoichiometric characteristics of the *P. arundinacea* in normal growth under no allelopathic stress from the *P. australis* is under the equilibrium state, measuring and calculating the contents of C, N, and P and ratios of C/N, C/P, and N/P in the leaves of the *P. arundinacea* respectively to obtain the ecological stoichiometric characteristics of the *P. arundinacea* under no allelopathic stress from the *P. australis* and the equilibrium state according the above methods; and measuring above-ground biomass per plant of the *P. arundinacea* under the equilibrium state at the same time; and then verifying the interference of different intensities of allelopathic stress (namely, different densities of the *P. australis*) on ecological stoichiometric equilibrium of the coexisting *P. arundinacea* and inhibition of different intensities of allelopathic stress on growth of the *P. arundinacea* by using the ecological stoichiometric characteristics and the biomass per plant of the *P. arundinacea* under the equilibrium state as controls respectively;

2) Characteristics of the Ecological Stoichiometric Equilibrium and Growth of *P. arundinacea* Under Different Intensities of Allelopathic Stress measuring the content of the total phenolic acids in the 0-30 cm soil layer in different plots respectively to quantitatively characterize the intensity of the allelopathic stress, measuring the contents of C, N, and P and the ratios of C/N, C/P, and N/P in the leaves of the *P. arundinacea* coexisting with the *P. australis* to quantitatively characterize the ecological stoichiometric characteristics of the *P. arundinacea* under different intensities of allelopathic stress, and measuring the above-ground biomass per plant of the *P. arundinacea* under different intensities of allelopathic stress at the same time; and 3) interference of different intensities of allelopathic stress on ecological stoichiometric equilibrium of *P. arundinacea* and inhibition of different intensities of allelopathic stress on growth of *P. arundinacea* under the following condition: a coefficient of variation (Cv) is statistically used to reflect a degree of dispersion of a group of data relative to an average of the group of data, and a formula of the coefficient of variation is:

$$Cv = \frac{s}{\bar{x}} \times 100\%, \text{ and}$$

$$s = \sqrt{\frac{\sum_{i=1}^{n}(x_i - \bar{x})^2}{n-1}} \ (i = 1, 2, 3, \ldots, n),$$

in the formula, Cv is the coefficient of variation, s and $\bar{x}$ are standard deviation and the average of the group of data respectively, $x_i$, is an i-th data in the group of data, and n is the number of data in the group; and during statistical analysis of the data, if the Cv exceeds 15%, the group of data is considered abnormal, and is excluded;

in the present invention, the interference of the allelopathic stress on the ecological stoichiometric equilibrium of the *P. arundinacea* requires clarification, and the equilibrium state is used as a contrast for the interference, and therefore, the present invention provides a concept of relative coefficient of variation (RCv) reflecting variation of the ecological stoichiometric characteristics after the interference relative to the ecological stoichiometric characteristics under the equilibrium state; and a formula is as follows:

$$RCv = \frac{S}{\bar{X}} \times 100\%, \text{ and}$$

$$S = \sqrt{\frac{\sum_{i=1}^{n}(X_i - \bar{X})^2}{N-1}} \ (i = 1, 2, 3, \ldots, n),$$

in the formula, RCv is the relative coefficient of variation, $X_1$ is an i-th data in an interfered group of data, N is the number of data in the interfered group, and $\bar{X}$ is an average of a control group of data; and in the method, the greater the RCv, the greater the interference of the allelopathic stress on the ecological stoichiometric equilibrium of the *P. arundinacea*, and the greater a degree of deviation from the equilibrium state, calculating RCvs of parameters including the contents of C, N, and P, and C/N, C/P, and N/P in the leaves of the *P. arundinacea* under different intensities of allelopathic stress relative to those in the leaves of the *P. arundinacea* under the equilibrium state respectively to reflect an interference degree of different intensities of allelopathic stress on the ecological stoichiometric equilibrium of the *P. arundinacea*; and then calculating RCvs of the above-ground biomass per plant of the *P. arundinacea* under different intensities of allelopathic stress relative to those of the *P. arundinacea* under the equilibrium state to reflect an inhibitory degree of different intensities of allelopathic stress on the growth of the *P. arundinacea*; and (4) verification of the allelopathic inhibition mechanism based on ecological stoichiometric equilibrium interference:

verifying whether the allelopathic inhibition mechanism based on the ecological stoichiometric equilibrium interference exists in combination with correlation analysis among parameters including the intensity of the allelopathic stress, the ecological stoichiometric equilibrium interference, and the growth inhibition according to an interference intensity of different intensities of allelopathic stress on the ecological stoichiometric equilibrium of the *P. arundinacea* and an inhibitory intensity of different intensities of allelopathic stress on the growth of the *P. arundinacea*, where if the interference intensity and the inhibitory intensity are great, a correlation among the three types of parameters is strong, the above new mechanism exists; otherwise, the new mechanism does not exist.

In summary, the present invention has the following beneficial effects.

The inhibition mechanism of allelopathic stress is complex and diverse. The present invention follows the main line of "content of allelochemicals, ecological stoichiometric equilibrium interference, and growth inhibition", uses the concept of RCv to characterize the interference degree of the allelopathic stress on an ecological stoichiometric ratio, and verifies whether an allelopathic inhibition mechanism based on the ecological stoichiometric equilibrium interference exists.

DETAILED DESCRIPTION OF THE EMBODIMENTS

An implementation site was located in the Zhenjiang Waterfront Wetlands along mid-lower reaches of the Yangtze River in China. This wetland was formed from the perennial accumulation of massive silt depositions carried by the river. A vegetation succession process of the wetland was as follows: a bare beach, a *P. arundinacea* community, a *P. arundinacea-P. australis* community, and a *P. australis* community. In the process that the *P. arundinacea* community was gradually replaced by the *P. australis* community, a density of the *P. australis* gradually increased till 40 plants/m$^2$, and the *P. arundinacea* disappeared. The following specific steps were performed.

1. Plot Selection

First, 2 plots were set with a density of the *P. australis* being 10-12 plants/m$^2$ and 24-26 plants/m$^2$ respectively from a *P. arundinacea-P. australis* community in waterfront wetlands according to the density of the *P. australis* from low to high, and represented two intensities of allelopathic stress from weak to strong respectively to be taken as two treatments, T1 and T2. Then, another plot was selected from a single *P. arundinacea* community as a control treatment (CK) under no allelopathic stress. 3 quadrats with an area of 1 m$^2$ were set in the above three plots as 3 repetitions.

2. Parameter Measurement

On April 24, samples for a series of parameter measurement and determination were taken from the waterfront wetlands.

Determination of contents of C, N, and P in leaves of the *P. arundinacea*: 5 *P. arundinacea* plants with uniform growth were selected in each quadrat, 5 unfolded leaves were acquired from top to bottom and taken back to a laboratory, and the contents of organic C, total N, and total P in the leaves were measured. The contents of C, N, and P were measured by potassium dichromate oxidation-spectrophotometry, Kjeldahl method, and alkali fusion-molybdenum antimony anti-spectrophotometry respectively.

Determination of biomass: 10 *P. arundinacea* plants with uniform growth were screened in each quadrat, above-ground parts were harvested, and fresh weight of the above-ground parts was weighed, and then average above-ground biomass per plant of the *P. arundinacea* was calculated.

Determination of a content of total phenolic acids in soil. 3 soil sampling points were selected in each quadrat, soil samples of 0-30 cm soil layer were drilled with soil at each soil sampling point since roots of the *P. arundinacea* were mostly distributed at the 0-30 cm soil layer, the soil samples were taken back to the laboratory, and the content of the total phenolic acids in soil was measured by phosphomolybdic acid phosphotungstate colorimetry.

3. Changes of Content of Total Phenolic Acids in Soil Under Different Densities of *P. australis*

Phenolic acid was one of the most common allelopathic substance, and the content of the phenolic acid in the soil was often used to characterize the intensity of the allelopathic stress. From the content of the total phenolic acids in the soil under different densities of the *P. australis* (that is, under different intensities of the allelopathic stress) (Table 1), it can be found that in the single *P. arundinacea* community without the *P. australis*, though there is a small amount of phenolic acids in the soil, with the invasion of the *P. australis* and the increase of its density, the content of the phenolic acids in the soil increases significantly. That is, the increase of the density of the *P. australis* has a significant effect on the increase of the content of the total phenolic acids in the soil, which shows that it is scientific and reasonable to use the difference of the density of the *P. australis* to characterize the intensity of the allelopathic stress.

TABLE 1

Content of total phenolic acids under different densities of *P. australis*

| Treatments | Density of *P. australis* (plant/m$^2$) | Total phenolic acids in soil |
|---|---|---|
| CK | 0 | 11.69a |
| T1 | 10-12 | 15.91b |
| T2 | 24-26 | 19.79c |

Note:
different lowercases indicate significant differences among different treatments ($P < 0.05$).

4. Analysis of Interference of Different Intensities of Allelopathic Stress on Ecological Stoichiometric Equilibrium of *P. arundinacea* and Inhibition of Different Intensities of Allelopathic Stress on Growth of *P. arundinacea*

It can be found from Table 2 that as the intensity of the allelopathic stress increases, the contents of C and N in the leaves of the *P. arundinacea* significantly increase, while that of P decreases, and stoichiometric ratios of C/P and N/P continue to rise, and a stoichiometric ratio of C/N fluctuates due to the difference in the increase of C and N. The above-ground biomass per plant of the *P. arundinacea* decreases significantly with an increase in the intensity of the allelopathic stress. This indicates that the allelopathic stress of the *P. australis* significantly interferes with the ecological stoichiometric equilibrium of the *P. arundinacea*, and then significantly inhibits its normal growth.

RCvs of parameters such as the ecological stoichiometric ratios and growth of the *P arundinacea* under different intensities of allelopathic stress are respectively calculated by using a formula of a relative coefficient of variation provided by the present invention to reflect an interference degree of different intensities of allelopathic stress on the ecological stoichiometric equilibrium of the *P. arundinacea* and an inhibitory degree of different intensities of allelopathic stress on the growth of the *P. arundinacea*.

(1) RCv of Content of C in *P. arundinacea* Under Different Intensities of Allelopathic Stress 1) T1 Treatment with Weaker Intensity of Allelopathic Stress Content of C: three repeated values of the content of C in the *P. arundinacea* in the CK treatment were 473.91 g·kg$^{-1}$, 468.34 g·kg$^{-1}$, and 471.14 g·kg$^{-1}$ respectively, and their average $\overline{X}$=471.13 g·kg$^{-1}$.

Three repeated values of the content of C in the *P. arundinacea* in the T1 treatment were 485.62 g·kg$^{-1}$, 491.20 g·kg$^{-1}$, and 492.46 g·kg$^{-1}$ respectively.

Standard Deviation:

$$S_{T1} = \sqrt{\frac{(485.62 - 471.13)^2 + (491.20 - 471.13)^2 + (492.46 - 471.13)^2}{3-1}}.$$

$$RCv(T1) = \frac{S_{T1}}{\bar{X}} \times 100\% = 4.91\%.$$

2) T2 Treatment with Stronger Intensity of Allelopathic Stress

Content of C: an average of the content of C in the *P. arundinacea* in the CK treatment was the same as above: $\bar{X} = 471.13$ g·kg$^{-1}$.

Three repeated values of the content of C in the *P. arundinacea* in the T2 treatment were 483.80 g·kg$^{-1}$, 499.87 g·kg$^{-1}$, and 486.92 g·kg$^{-1}$.

Standard Deviation:

$$S_{T2} = \sqrt{\frac{(483.80 - 471.13)^2 + (499.87 - 471.13)^2 + (486.92 - 471.13)^2}{3-1}}.$$

$$RCv(T2) = \frac{S_{T2}}{\bar{X}} \times 100\% = 5.28\%.$$

(2) RCvs of Contents of N and P, and Ratios of C/N, C/P, and N/P in *P. arundinacea* and Above-Ground Biomass Per Plant of *P. arundinacea* Under Different Intensities of Allelopathic Stress The calculation method of the RCvs of these parameters was the same as above, and specific values are shown in Table 2. Results show that as the intensity of the allelopathic stress increases, RCvs of various ecological stoichiometric parameters and the above-ground biomass per plant of the *P. arundinacea* all significantly increase, which indicates that the ecological stoichiometric equilibrium interference of the *P. arundinacea* and the inhibition on the growth of the *P. arundinacea* are increasingly obvious with the increase of the intensity of the allelopathic stress. While under the stronger intensity of the allelopathic stress, the RCvs of the stoichiometric parameters such as the content of N and the ratios of C/P and N/P and the above-ground biomass per plant of the *P. arundinacea* are even more than 15%, which indicates that an interference degree of the allelopathic stress on the ecological stoichiometric equilibrium of the *P arundinacea* and an inhibitory degree of the allelopathic stress on the growth of the *P arundinacea* are strong.

TABLE 2

Contents of C, N, and P and their stoichiometric ratio characteristics in leaves of *P. arundinacea* under different densities of *P. australis*

| Treatments | N (g · kg$^{-1}$) | P (g · kg$^{-1}$) | C/N | C/P | N/P | Biomass (g/plant) |
|---|---|---|---|---|---|---|
| CK | 32.58a | 2.50b | 14.46b | 188.45a | 13.03a | 11.38a |
| T1 | 33.54b | 2.40b | 14.60b | 204.07ab | 13.98a | 10.74b |
| T2 | 37.80c | 2.28a | 12.97a | 215.00b | 16.58b | 9.02 c |
| RCv (T1) | 3.74 | 5.27 | 2.36 | 10.34 | 8.76 | 6.77 |
| RCv (T2) | 19.64 | 11.71 | 13.06 | 17.44 | 33.33 | 24.07 |

Note:
RCv represents a relative coefficient of variation relative to CK, and different lowercases indicate significant differences among different treatments (P < 0.05).

5. Verification of the Allelopathic Inhibition Mechanism Based on Ecological Stoichiometric Equilibrium Interference The inhibition mechanism of the allelopathic stress is complex and diverse. Through the correlation analysis among parameters including the content of the total phenolic acids in the soil (different intensities of allelopathic stress), the ecological stoichiometric equilibrium interference of the *P. arundinacea*, and the growth inhibition (Table 3), it can be found that the content of the total phenolic acids in the plot soil is not only significantly correlated (positively or negatively) with C, P, and C/N of the *P. arundinacea*, but also extremely significantly positively correlated with N, C/P, and N/P, and extremely significantly negatively correlated with the biomass, and the biomass has a significant or extremely significant correlation with various ecological stoichiometric parameters except C, which indicates that the phenolic acid inhibits the growth of the *P. arundinacea* by interfering with its ecological stoichiometric equilibrium. Therefore, the allelopathic inhibition mechanism based on the ecological stoichiometric equilibrium interference can be finally verified by using the *P. australis* and the *P. arundinacea* as experimental materials and using the method provided by the present invention.

TABLE 3

Correlation analysis among content of total phenolic acids in soil, ecological stoichiometric characteristics of leaves of *P. arundinacea* and above-ground biomass per plant of *P. arundinacea*

|  | Total phenolic acids in soil | C | N | P | C/N | C/P | N/P | Biomass |
|---|---|---|---|---|---|---|---|---|
| Total phenolic acids in soil | 1 | | | | | | | |
| C | 0.791* | 1 | | | | | | |
| N | 0.925** | 0.573 | 1 | | | | | |
| P | −0.782* | −0.630 | −0.711* | 1 | | | | |
| C/N | −0.787* | −0.306 | −0.955** | 0.589 | 1 | | | |
| C/P | 0.856** | 0.790* | 0.746* | −0.972** | −0.575 | 1 | | |
| N/P | 0.923** | 0.622 | 0.949** | −0.895** | −0.874** | 0.900** | 1 | |
| Biomass | −0.954** | −0.640 | −0.982** | 0.735* | 0.908** | −0.779* | −0.942** | 1 |

Note:
*indicates significant correlation ($P < 0.05$); and
**indicates extremely significant correlation ($P < 0.01$).

What is claimed is:

1. A verification method of an allelopathic inhibition mechanism based on ecological stoichiometric equilibrium interference, comprising the following steps:

1) plot selection, comprising the step of:
selecting 2-3 plots with different *P. australis* density from a *P. arundinacea-P. australis* community in Zhenjiang Waterfront Wetlands along mid-lower reaches of the Yangtze River in China according to a density of *P. australis* from low to high, wherein the plots represent different intensities of allelopathic stress exerted by the *P. australis* on *P. arundinacea* from weak to strong respectively; then selecting another plot from a single *P. arundinacea* community as a control under no allelopathic stress; and setting 3 quadrats with an area of 1 m² in each of the plots as 3 repetitions;

2) parameter measurement, comprising the steps of:
conducting a parameter measurement in late April when both the *P. arundinacea* and the *P. australis* are in a vigorous growth period, and the allelopathic stress of the *P. australis* on the *P. arundinacea* is most obvious at the vigorous growth period, wherein measurement parameters comprise a content of phenolic acid allelochemicals released from an allelopathic donor of the *P. australis* into soil, contents of organic carbon (C), nitrogen (N), and total phosphorus (P) in leaves of an allelopathic receptor plant of the *P. arundinacea*, and an above-ground biomass per plant of the *P. arundinacea*, wherein
determination of the contents of C, N, and P in the leaves of the *P. arundinacea* comprises the steps of: selecting 5-7 of *P. arundinacea* plants with uniform growth in each quadrat, acquiring 3-5 unfolded leaves from top to bottom, taking the unfolded leaves back to a laboratory, and measuring the contents of C, N, and P in the unfolded leaves, wherein the contents of organic C, total N, and total P are respectively measured by potassium dichromate oxidation-spectrophotometry, Kjeldahl method, and alkali fusion-molybdenum antimony anti-spectrophotometry;

wherein determination of the above-ground biomass per plant of the *P. arundinacea* comprises the steps of: selecting another 8-10 of the *P. arundinacea* plants with uniform growth in each quadrat, harvesting above-ground parts and weighing fresh weight of the above-ground parts, and then calculating an average above-ground biomass per plant of the *P. arundinacea*, wherein the above-ground biomass per plant of the *P. arundinacea* under the different intensities of the allelopathic stress is obtained; and wherein determination of a content of total phenolic acid allelochemicals in the soil comprises the steps of: taking 3-5 soil sampling points in each quadrat, drilling soil samples from a 0-30 cm soil layer with soil at each of the soil sampling points where roots of the *P. arundinacea* are mostly distributed, taking the soil samples back to the laboratory, and measuring the content of the total phenolic acid allelochemicals in the soil by phosphomolybdic acid phosphotungstate colorimetry;

3) analysis of the ecological stoichiometric equilibrium interference, comprising the step of:
a) analyzing characteristics of the ecological stoichiometric equilibrium and a growth of *P. arundinacea* under equilibrium state, comprising the step of:
wherein under the following condition: in the single *P. arundinacea* community where ecological stoichiometric characteristics of the *P. arundinacea* in normal growth under no allelopathic stress from the *P. australis* is under the equilibrium state, measuring and calculating the contents of C, N, and P and ratios of C/N, C/P, and N/P in the leaves of the *P. arundinacea* respectively to obtain the ecological stoichiometric characteristics of the *P. arundinacea* under no allelopathic stress from the *P. australis* and the equilibrium state according to the determination of the contents of C, N, and P in the leaves of the *P. arundinacea* of the parameter measurement of step (2); and measuring the above-ground biomass per plant of the *P. arundinacea* under the equilibrium state at the same time; and then verifying an interference of the different intensities of the allelopathic stress, wherein the allelopathic stress is different densities of the *P. australis*, on the ecological stoichiometric equilibrium of coexisting *P. arundinacea* and inhibition of the different intensities of the allelopathic stress on growth of the *P. arundinacea* by using the ecological stoichiometric characteristics and the above-ground biomass per plant of the *P. arundinacea* under the equilibrium state as controls respectively;
b) analyzing characteristics of the ecological stoichiometric equilibrium and the growth of the *P. arundinacea* under the different intensities of the allelopathic stress, comprising the step of:
measuring the content of the total phenolic acid allelochemicals in the 0-30 cm soil layer in the plots respectively to quantitatively characterize an intensity of the allelopathic stress, measuring the contents of organic C, total N, and total P and the ratios of C/N, C/P, and N/P in the unfolded leaves of the *P. arundinacea* coexisting with the *P. australis* to quantitatively characterize the ecological stoichiometric characteristics of the *P. arundinacea* under the different intensities of the allelopathic stress; and measuring the above-ground biomass per plant of the *P. arundinacea* under different intensities of allelopathic stress at the same time; and c) analyzing the interference of the different intensities of the allelopathic stress on the ecological stoichiometric equilibrium of the *P. arundinacea* and the inhibition of the different intensities of the allelopathic stress on the growth of *P. arundinacea*, comprising the steps of:

wherein under the following condition: using a coefficient of variation (Cv) to statistically reflect a degree of dispersion of a group of data relative to an average of the group of data, and a formula of the coefficient of variation is:

$$Cv = \frac{s}{\bar{x}} \times 100\%, \text{ and}$$

$$s = \sqrt{\frac{\sum_{i=1}^{n}(x_i - \bar{x})^2}{n-1}} \ (i = 1, 2, 3, \ldots, n),$$

wherein Cv is the coefficient of variation, s and $\bar{x}$ are standard deviation and the average of the group of data respectively, $x_i$ is an i-th data in the group of data, and n is the number of data in the group of data; and during statistical analysis of the group of data, if the Cv exceeds 15%, the group of data is considered abnormal, and is excluded;

wherein the interference of the allelopathic stress on the ecological stoichiometric equilibrium of the *P. arundinacea* requires clarification, and the equilibrium state is used as a contrast for the interference, and a relative coefficient of variation (RCv) reflects a variation of the ecological stoichiometric characteristics after the interference relative to the ecological stoichiometric characteristics under the equilibrium state; and a formula is as follows:

$$RCv = \frac{S}{\bar{X}} \times 100\%, \text{ and}$$

$$S = \sqrt{\frac{\sum_{i=1}^{n}(X_i - \bar{X})^2}{N-1}} \ (i = 1, 2, 3, \ldots, n),$$

wherein RCv is the relative coefficient of variation, $X_i$ is an i-th data in an interfered group of data, N is a number of data in the interfered group, and $\bar{X}$ is an average of a control group of data; and the greater the RCv, the greater the interference of the allelopathic stress on the ecological stoichiometric equilibrium of the *P. arundinacea*, and the greater a degree of deviation from the equilibrium state, calculating RCvs of parameters comprising the contents of organic C, total N, and total P, and the ratios of C/N, C/P, and N/P in the leaves of the *P. arundinacea* under the different intensities of the allelopathic stress relative to the contents of organic C, total N, and total P, and the ratios of C/N, C/P, and N/P in the leaves of the *P. arundinacea* under the equilibrium state respectively to reflect an interference degree of the different intensities of the allelopathic stress on the ecological stoichiometric equilibrium of the *P. arundinacea*; and then calculating RCvs of the above-ground biomass per plant of the *P. arundinacea* under the different intensities of the allelopathic stress relative to the above-ground biomass per plant of the *P. arundinacea* under the equilibrium state to reflect an inhibitory degree of the different intensities of the allelopathic stress on the growth of the *P. arundinacea*; and 4) verification of the allelopathic inhibition mechanism based on the ecological stoichiometric equilibrium interference, comprising the steps of:

verifying whether the allelopathic inhibition mechanism based on the ecological stoichiometric equilibrium interference exists in combination with a correlation analysis among three types of parameters comprising the intensity of the allelopathic stress, the ecological stoichiometric equilibrium interference, and a growth inhibition according to the interference degree of the different intensities of the allelopathic stress on the ecological stoichiometric equilibrium of the *P. arundinacea* and the inhibitory degree of the different intensities of the allelopathic stress on the growth of the *P. arundinacea*, wherein if the interference degree and the inhibitory degree are greater than 15%, a correlation among the three types of parameters is strong, the allelopathic inhibition mechanism exists; otherwise, the allelopathic inhibition mechanism does not exist.

\* \* \* \* \*